(12) United States Patent
Swift

(10) Patent No.: US 8,979,745 B2
(45) Date of Patent: Mar. 17, 2015

(54) LARYNGOSCOPE HANDLE

(71) Applicant: OBP Medical Corporation, Lawrence, MA (US)

(72) Inventor: Jeffrey Ralph Swift, Tewksbury, MA (US)

(73) Assignee: OBP Medical Corporation, Lawrence, MA (US)

( * ) Notice: Subject to any disclaimer, the term of this patent is extended or adjusted under 35 U.S.C. 154(b) by 77 days.

(21) Appl. No.: 13/967,366

(22) Filed: Aug. 15, 2013

(65) Prior Publication Data
US 2015/0051447 A1    Feb. 19, 2015

(51) Int. Cl.
*A61B 1/267*    (2006.01)

(52) U.S. Cl.
CPC ..................................... *A61B 1/267* (2013.01)
USPC ......................................................... 600/185

(58) Field of Classification Search
USPC .......................................................... 600/185
See application file for complete search history.

(56) References Cited

U.S. PATENT DOCUMENTS 5,209,475 A * 5/1993 Loman ........................... 473/294
2012/0330103 A1 * 12/2012 Tenger et al. ................. 600/188

* cited by examiner

*Primary Examiner* — Sameh Boles
(74) *Attorney, Agent, or Firm* — CKC & Partners Co., Ltd.

(57) ABSTRACT

A laryngoscope comprises a blade portion and a handle portion. The handle portion comprises a plurality of grip portions, a bottom support and a top support, a bottom support and a top support. The grip portions are separated form each other. One end of each of the grip portions is mounted on the bottom support, and the other end of each of the grip portions is mounted on the top support. The blade portion is integrally formed with the top support of the handle portion and extending away from the handle portion. Each of the grip portions is formed by a two-part mold technique.

10 Claims, 5 Drawing Sheets

LARYNGOSCOPE HANDLE

BACKGROUND

1. Field of Invention

The present invention relates to a laryngoscope, and more particularly to a laryngoscope handle.

2. Description of Related Art

Health care providers perform direct laryngoscopy to either clear a to patient's airway of debris, or place an endotracheal tube into a patient's trachea to assist or replace a patient's ability to oxygenate his/her system. The laryngoscope utilizes either a lighted straight or curved blade that allows visualization of the vocal cords, indicating the opening of the trachea. This lighted blade is used to keep the tongue from obstructing the medical provider's view of the vocal cords. The tip of the blade lifts the epiglottis, thereby providing a direct view into the patient's trachea, and reducing the risk of intubating the esophagus instead.

Existing laryngoscopes have round handles. These handles often become contaminated with blood, vomit, or other fluids from the patient or from the environment. These fluids will reduce the contact resistance between the operator's hand and the laryngoscope, and make the laryngoscope difficult to hold during use. Laryngoscopes are often sold with single use blades and re-usable handles. A single use blade has the advantage of not requiring cleaning or other preparation prior to use. Because of contamination it is advantageous for the handle to also be single use, but round handles require more complex molding and forming operations, and due to manufacturing complexity and expense round handles are typically not offered in a single use form.

SUMMARY

Embodiments of the present invention provide a laryngoscope handle which is easy to hold during use.

Embodiments of the present invention also provide areas in the handle to displace fluid to ensure that the laryngoscope can be securely held.

The present invention provides a laryngoscope which comprises a blade portion and a handle portion. The handle portion comprises a first grip portion, a second grip portion and a third grip portion, a bottom support and a top support. The first grip portion, the second grip portion and the third grip portion are separated from each other. One end of each of the first, second and third grip portions is mounted on the bottom support, and the other end of each of the first, second and third grip portions is mounted on the top support. The blade portion is integrally formed with the top support of the handle portion and extending away from the handle portion.

In an embodiment, the first grip portion has a first surface facing away from the second and third grip portions, and a second surface opposite to the first surface. The first surface of the first grip portion has a waved shape including a plurality of outwardly extending peaks and a plurality of inwardly extending valleys, wherein the inwardly extending valleys in the first surface define upper finger rest regions each for receiving a portion of one of the fingers of an operator.

In an embodiment, the second grip portion has a first surface facing the second surface of the first grip portion and a second surface opposite to the first surface, wherein the first surface and the second surface of the second grip portion are flat.

The second grip portion further comprises two sides perpendicular to the first surface and the second surface of the second grip portion, wherein each side of the second grip portion has a waved shape that has a plurality of outwardly extending peaks and a plurality of inwardly extending valleys. The inwardly extending valleys in each side of the second grip portion define lower to finger rest regions each for receiving a portion of one of the fingers of the operator.

In an embodiment, the third grip portion has a first surface facing the second surface of the second grip portion and a second surface opposite to the first surface, the first surface and the second surface of the third grip portion are flat, and the second surface of the third grip portion defines a palm rest region on which the palm of the operator can be placed.

In an embodiment, a width of the second grip portion is larger than that of the first grip portion.

In an embodiment, a width of the second grip portion is larger than that of the third grip portion.

In an embodiment, the blade portion further comprises a cavity for receiving a light source. The blade portion further comprises a removable tab. The removable tab interrupts an electrical connection between the light source and a battery, wherein when the removable tab is removed from the blade portion, the light source and the battery are electrically connected.

In an embodiment, each of the three grip portions is formed by a two-part mold technique.

Accordingly, the present invention allows fluid generated during medical procedures to flow into the areas away from where the operator's hand contacts the handle portion. This makes the contact areas less slippery, and as a result, the handle portion can be held on more securely by the operator.

BRIEF DESCRIPTION OF THE DRAWINGS

In order to make the foregoing as well as other aspects, features, advantages, and embodiments of the present invention more apparent, the accompanying drawings are described as follows.

DETAILED DESCRIPTION

Figure 1:
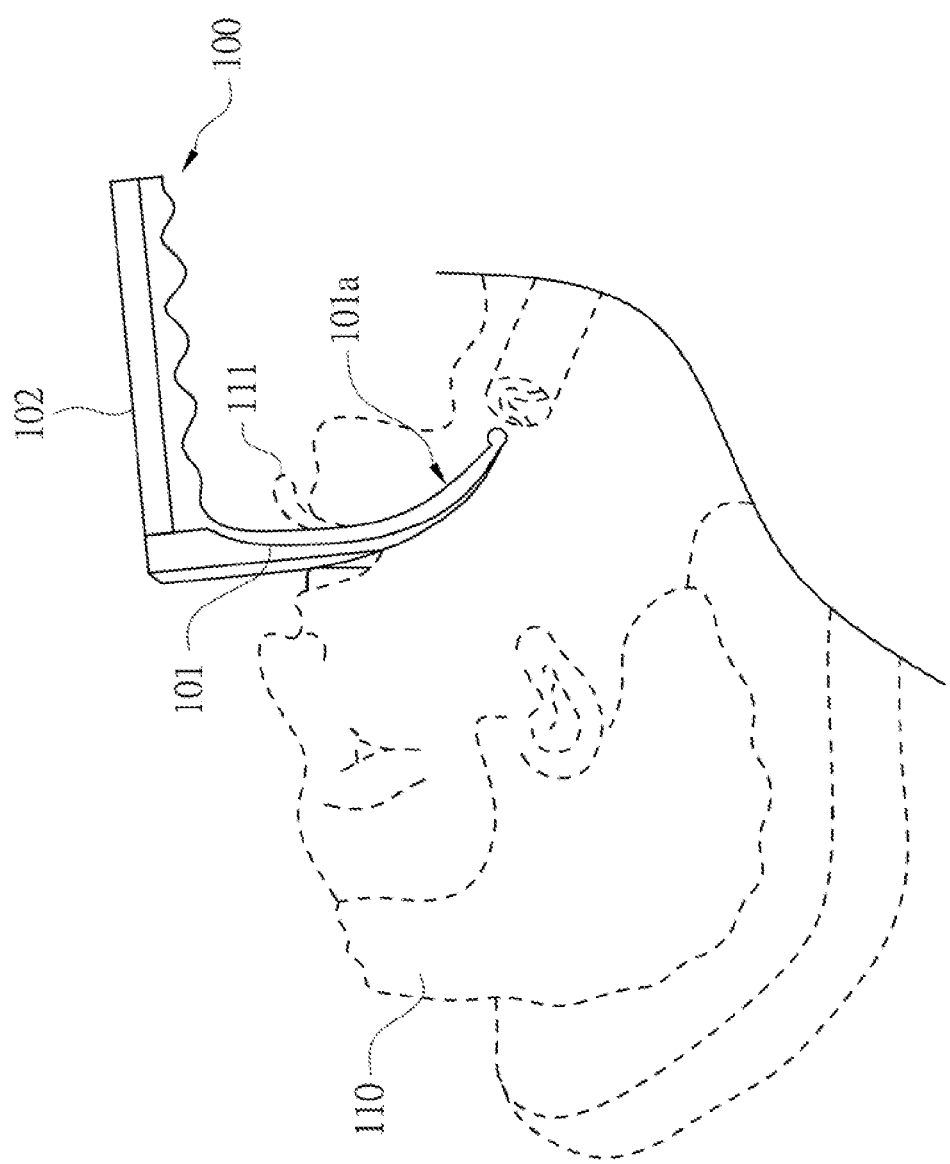
FIG. 1 is a schematic diagram of a laryngoscope being used to view a patient's larynx.

Reference will now be made in detail to the present embodiments of the invention, examples of which are illustrated in the accompanying drawings. Wherever possible, the same reference numbers are used in the drawings and the description to refer to the same or like parts.

FIG. 1 is a schematic diagram of a laryngoscope being used to view a patients larynx. In FIG. 1, the laryngoscope 100 is shown placed in the mouth of a patient 110 for viewing the vocal cords adjacent the larynx. The laryngoscope 100 includes a blade portion 101 and a handle portion 102. The blade portion 101 is used to hold the patient's tongue 111 out of the way for viewing the vocal cords.

Figure 2:
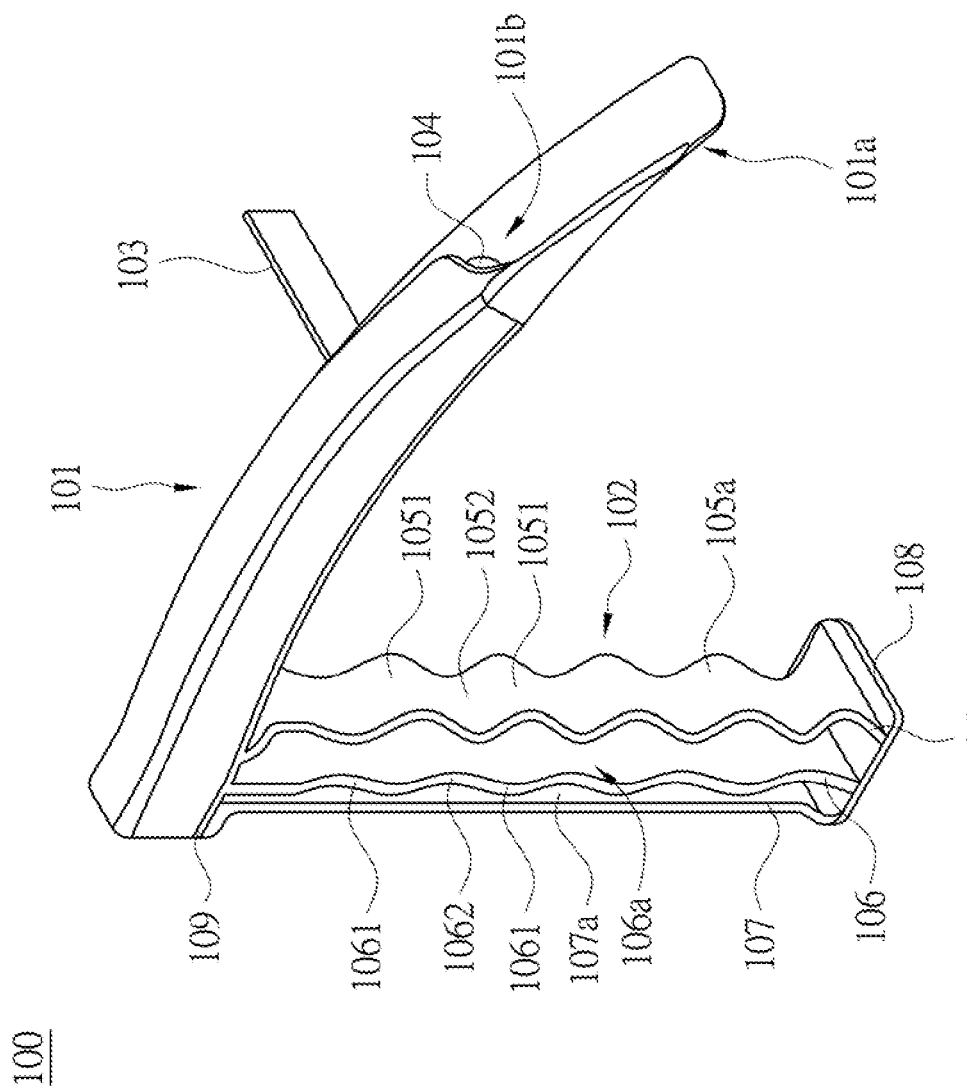
FIG. 2 is a left perspective view of the laryngoscope of FIG. 1.
Figure 3:
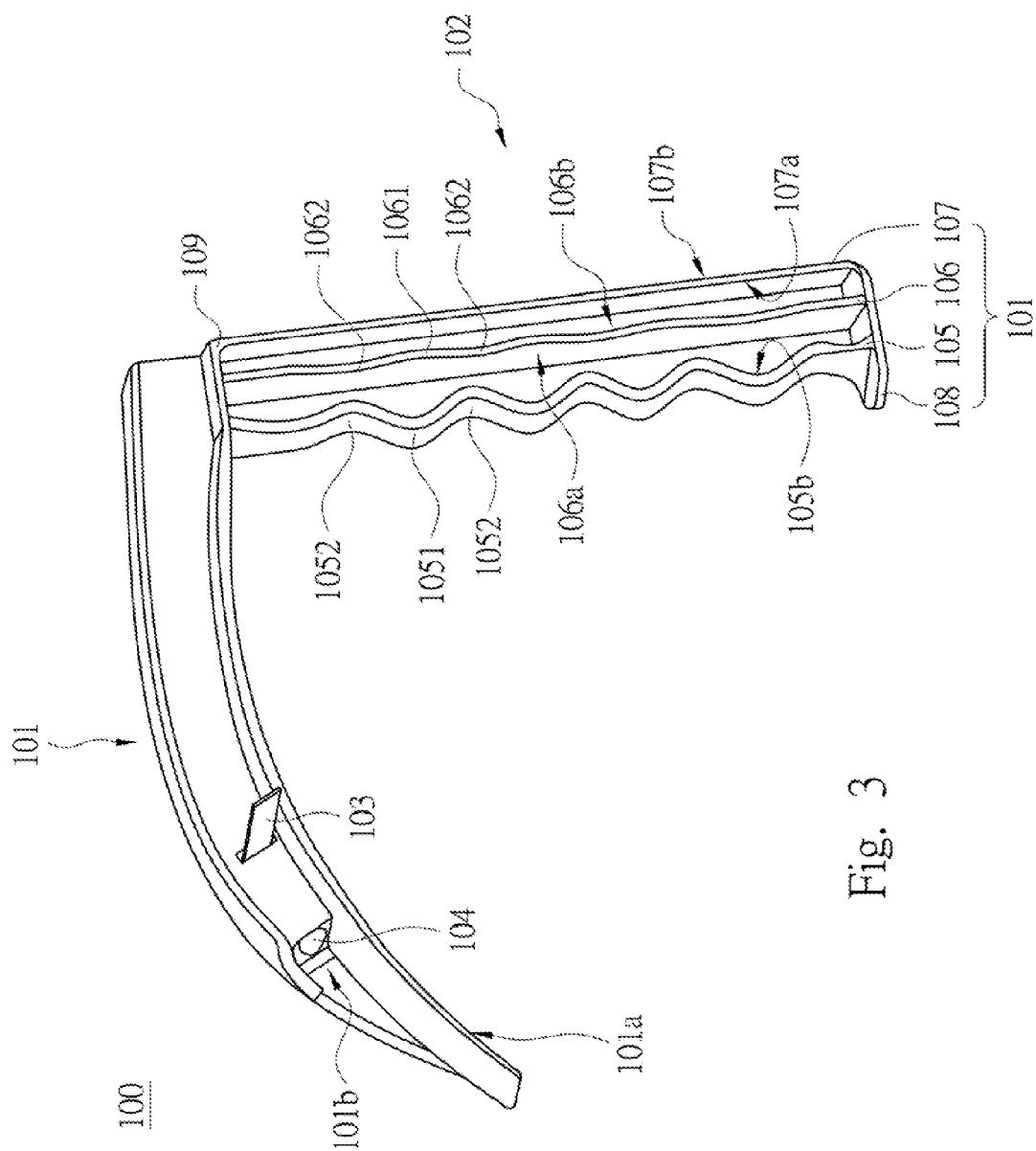
FIG. 3 is a right perspective view of the laryngoscope of FIG. 1.
Figure 4:
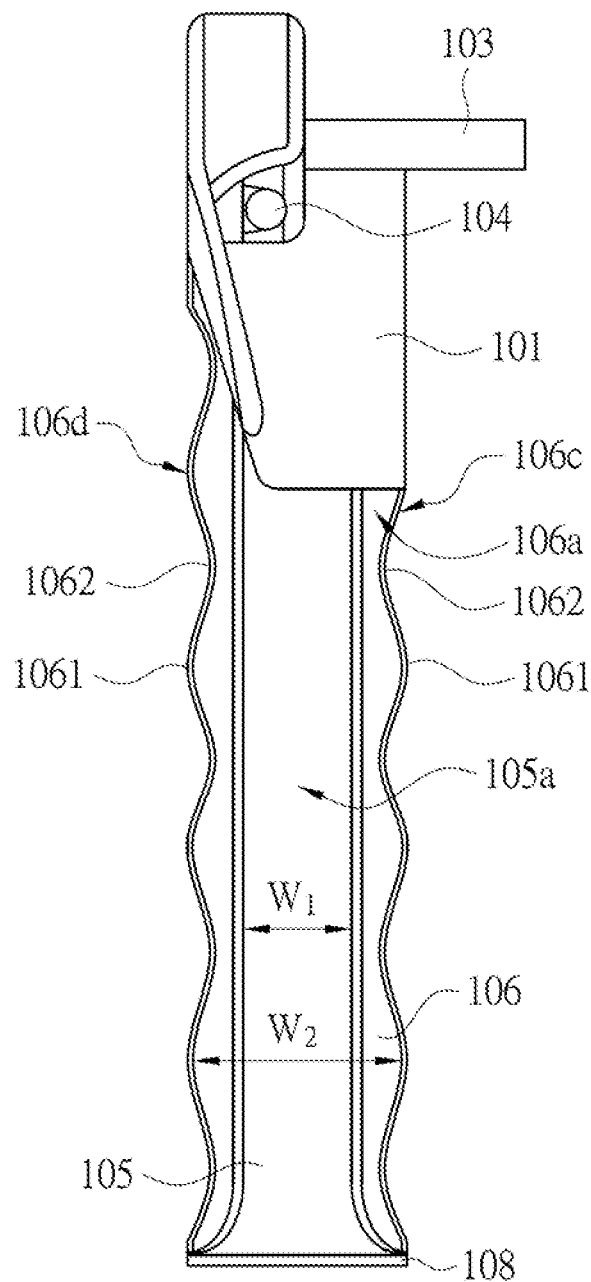
FIG. 4 is a front view of the laryngoscope of FIG. 1.
Figure 5:
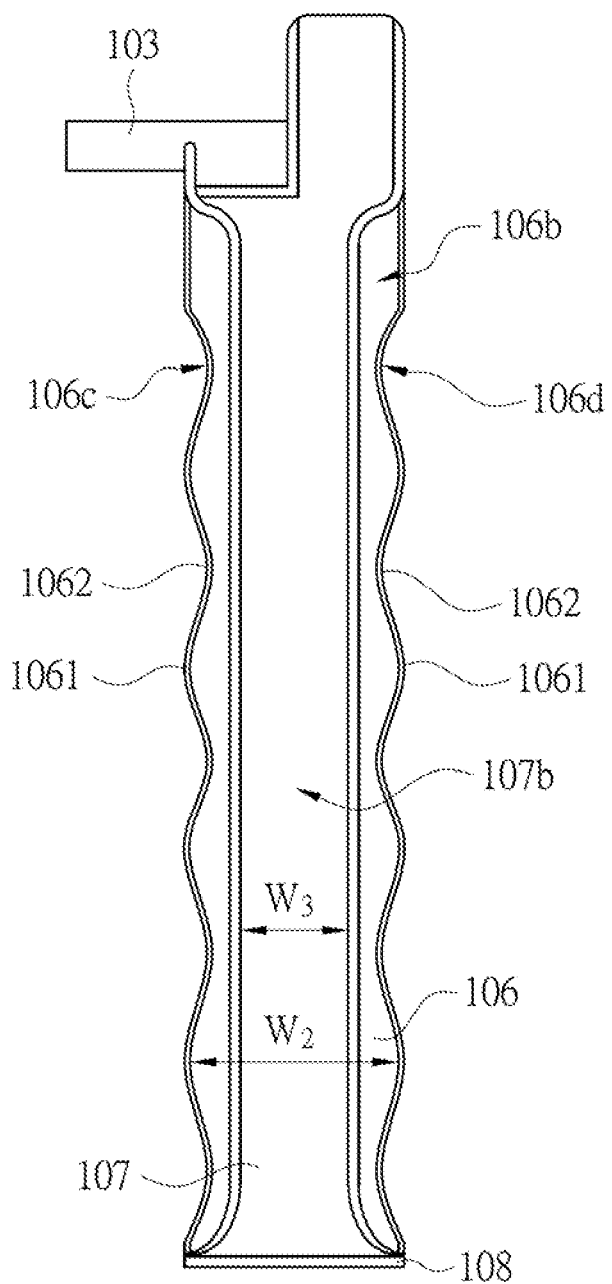
FIG. 5 is a rear view of the laryngoscope of FIG. 1.

FIG. 2 is a left perspective view of the laryngoscope of FIG. 1. FIG. 3 is a right perspective view of the laryngoscope of FIG. 1. FIG. 4 is a front view of the laryngoscope of FIG. 1. FIG. 5 is a rear view of the laryngoscope of FIG. 1.

With reference to FIG. 2 to FIG. 5, the laryngoscope 100 comprises the blade portion 101 and the handle portion 102. The handle portion 102 has an end. In some embodiments, the blade portion 101 is integrally formed with the end of the handle portion 102 and extends away from the handle portion 102. The blade portion 101 and the handle portion 102 form an angle of about 90 degrees but other angles are possible as well. In some embodiments, the handle portion 102 is made of plastic. Many different kinds of plastic materials may be used, and those skilled in the art would be able to choose suitable materials as needed. The blade portion 101 has a curved surface 101a so as to correspond to the upper surface of the patient's tongue 111. The blade portion 101 is used to hold the patient's tongue 111 down.

The blade portion 101 includes a cavity 101b for receiving a light source 104. In an embodiment, the light source 104 includes a battery (not shown) that is disposed in the cavity 101b. An electrical connection between the light source 104 and the battery is interrupted by a removable tab 103. When the removable tab 103 is removed from the blade portion 101, the light source 104 is electrically connected to the battery, resulting in illumination of the light source 104. That is, the light source 104 of the laryngoscope 100 is switched on by removing the removable tab 103. Once activated, the light source 104 will remain illuminated for a fixed time. Once the light source 104 becomes deactivated, and the light source 104 no longer illuminates, the laryngoscope 100 cannot be reused on another patient as the light source 104 can no longer be activated. The entire unit of the laryngoscope 100 is then disposed of.

The handle portion 102 includes a plurality of grip portions. In this embodiment, the handle portion 102 includes three grip portions, namely, a first grip portion 105, a second grip portion 106 and a third grip portion 107. However, in another embodiment, the handle portion 102 may include two grip to portions or more than three grip portions. The handle portion 102 further includes a bottom support 108 and a top support 109. One end of each grip portion 105, 106 and 107 is mounted on the bottom support 108, and the other end of each grip portion 105, 106 and 107 is mounted on the top support 109. The blade portion 101 is attached to the top support 109. When the distances among the first, second and third grip portions 105, 106 and 107 are increased, the area of the top support 109 must be enlarged to accommodate the first, second and third grip portions 105, 106 and 107. Through such a configuration, the contact area between the blade portion 101 and the handle portion 102 is increased. Accordingly, the discrete three grip portion design (of the first, second and third grip portions 105, 106 and 107) can provide a greater contact area between the blade portion 101 and the handle portion 102. This greater contact area significantly increases the strength of the laryngoscope 100.

As described above, the three grip portions 105, 106 and 107 are separated from each other. Fluid is normally present during medical procedures, and this fluid makes the laryngoscope 100 slippery. However, such a discrete grip portion design allows the fluid to flow into the area between the first and second grip portions 105, 106 or the area between the second and third grip portions 106, 107, that is, away from the areas where the operators hand contacts the grip portions 105, 106 and 107. This makes the contact areas less slippery and therefore allows the laryngoscope 100 to be operated more securely.

In an embodiment, the first grip portion 105 has a first surface 105a facing away from the second and third grip portions 106, 107, and a second surface 105b opposite to the first surface 105a. The first surface 105a has a waved or sinusoidal shape including a plurality of outwardly extending peaks 1051 and a plurality of inwardly extending valleys 1052. The inwardly extending valleys 1052 in the first surface 105a define upper finger rest regions each for receiving a portion of one of the fingers of the operator. The waved or sinusoidal shape helps the operator to securely hold the laryngoscope 100. Moreover, because fluid generated during medical procedures is able to flow to the second surface 105b, which the operator does not contact, the first surface 105a that the operator does contact is made less slippery and therefore can be held onto more securely by the operator.

The second grip portion 106 is arranged behind the first grip portion 105. The width W2 of the second grip portion 106 is larger than the width W1 of the first grip portion 105. The second grip portion 106 has a first surface 106a facing the second surface 105b of the first grip portion 105 and a second surface 106b opposite to the first surface 106a. The first surface 106a and the second surface 106b are flat. However, each of the sides 106c and 106d perpendicular to the first surface 106a and the second surface 106b has a waved or sinusoidal shape that has a plurality of outwardly extending peaks 1061 and a plurality of inwardly extending valleys 1062. The inwardly extending valleys 1062 in the sides 106c and 106d define lower finger rest regions each for receiving a portion of one of the fingers of the operator. The waved or sinusoidal shape helps the operator to securely hold the laryngoscope 100. Moreover, fluid generated during medical procedures is able to flow to the first surface 106a and the second surface 106b, which the operator does not contact. Therefore, the sides 106c and 106d that the operator does contact are made less slippery and as a result can be held onto more securely by the operator.

The third grip portion 107 is arranged behind the second grip portion 106. The width W2 of the second grip portion 106 is lamer than the width W3 of the third grip portion 107. The third grip portion 107 has a first surface 107a facing the second surface 106b of the second grip portion 106 and a second surface 107b opposite to the first surface 107a. The first surface 107a and the second surface 107b of the third grip portion 107 are flat. The second surface 107b of the third grip portion 107 defines a palm rest region on which the palm of the operator can be placed. Fluid generated during medical procedures may flow to the first surface 107a, which the operator does not contact. Therefore, the second surface 107b that the operator does contact is made less slippery and as a result can be held onto more securely by the operator.

When holding the laryngoscope 100, the operator grips each of the three grip portions 105, 106 and 107 with one hand and in such a manner that the palm is in contact with the palm rest region of the second surface 107b, and the fingers are in contact with (i.e., partially received in) the lower finger rest regions of the inwardly extending valleys 1062 in the side 106c or 106d, and the upper finger rest regions of the inwardly extending valleys 1052 in the first surface 105a.

It is noted that each grip portion 105, 106 or 107 can be molded utilizing a two-part mold technique. The use of molding techniques allows the entire laryngoscope 100 to be single-use.

The handle according to embodiments of the present invention provides comfort. Moreover, the configuration of the embodiments of the present invention described above is such that fluid generated during medical procedures flows to areas away from where the operator's hand contacts the to handle portion 102 of the laryngoscope 100 so that the handle portion 102 is made less slippery for the operator.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A laryngoscope, comprising: a blade portion; and a handle portion comprising a plurality of grip portions, a bottom support and a top support, wherein the grip portions are separated from each other, and the grip portions comprises a first grip portion, a second grip portion and a third grip portion, one end of each of the first, second and third grip portions is mounted on the bottom support, and the other end of each of the first, second and third grip portions is mounted on the top support, and the blade portion is integrally formed with the top support of the handle portion and extending away from the handle portion.

2. The laryngoscope of claim 1, wherein the first grip portion has a first surface facing away from the second and third grip portions, and a second surface opposite to the first surface, the first surface of the first grip portion has a waved shape including a plurality of outwardly extending peaks and a plurality of inwardly extending valleys, and the inwardly extending valleys in the first surface define upper finger rest regions each for receiving a portion of one of the fingers of an operator.

3. The laryngoscope of claim 2, wherein the second grip portion has a first surface facing the second surface of the first grip portion and a second surface opposite to the first surface, and the first surface and the second surface of the second grip portion are flat.

4. The laryngoscope of claim 3, wherein the second grip portion further comprises two sides perpendicular to the first surface and the second surface of the second grip portion, each side of the second grip portion has a waved shape that has a plurality of outwardly extending peaks and a plurality of inwardly extending valleys, and the inwardly extending valleys in each side of the second grip portion define lower finger rest regions each for receiving a to portion of one of the fingers of the operator.

5. The laryngoscope of claim 3, wherein the third grip portion has a first surface facing the second surface of the second grip portion and a second surface opposite to the first surface, the first surface and the second surface of the third grip portion are flat, and the second surface of the third grip portion defines a palm rest region on which the palm of the operator can be placed.

6. The laryngoscope of claim 1, wherein a width of the second grip portion is larger than a width of the first grip portion.

7. The laryngoscope of claim 1, wherein a width of the second grip portion is larger than a width of the third grip portion.

8. The laryngoscope of claim 1, wherein the blade portion further comprises a cavity for receiving a light source.

9. The laryngoscope of claim 8, wherein the blade portion further comprises a removable tab, the removable tab interrupts an electrical connection between the light source and a battery, and when the removable tab is removed from the blade portion, the light source and the battery are electrically connected.

10. The laryngoscope of claim 1, wherein each of the three grip portions is formed by a two-part mold technique.

\* \* \* \* \*